(12) United States Patent
Murthy et al.

(10) Patent No.: US 9,017,485 B2
(45) Date of Patent: Apr. 28, 2015

(54) ICE DISPENSING AND CLEANING MECHANISM AND PROCESS

(71) Applicant: Cornelius, Inc., St. Paul, MN (US)

(72) Inventors: Vittal Murthy, Bangalore (IN); Jayateertha Malagi, Karnataka (IN); Servesh Adderi Raganath, Karnataka (IN); Matthew Kampert, Lombard, IL (US); Chris Zemko, Elgin, IL (US)

(73) Assignee: Cornelius, Inc., St. Paul, MN (US)

( * ) Notice: Subject to any disclaimer, the term of this patent is extended or adjusted under 35 U.S.C. 154(b) by 0 days.

(21) Appl. No.: 13/956,940

(22) Filed: Aug. 1, 2013

(65) Prior Publication Data

US 2014/0158165 A1    Jun. 12, 2014

Related U.S. Application Data

(60) Provisional application No. 61/678,194, filed on Aug. 1, 2012.

(51) Int. Cl.
| | |
|---|---|
| B08B 7/04 | (2006.01) |
| B67D 1/07 | (2006.01) |
| A61L 2/00 | (2006.01) |
| G05B 17/00 | (2006.01) |
| B08B 9/093 | (2006.01) |
| F25C 5/00 | (2006.01) |

(52) U.S. Cl.
CPC ... *B67D 1/07* (2013.01); *A61L 2/00* (2013.01); *G05B 17/00* (2013.01); *B08B 9/093* (2013.01); *B08B 9/0936* (2013.01); *F25C 5/002* (2013.01)

(58) Field of Classification Search
CPC ........ A23G 9/30; B60H 3/0085; B65D 83/34; B67D 1/07; B67D 3/0009; B67D 1/0857; B08B 1/00; B08B 3/00; B08B 3/02; B08B 3/024; B08B 3/04; B08B 9/00; B08B 9/02; B08B 9/027; B08B 9/08; B08B 9/0813; B08B 7/0092; B08B 9/093; B08B 9/0936; F25C 5/002; A61L 2/18; A61L 2/24
USPC .............. 62/78, 264, 303; 422/28; 222/146.6, 222/148; 134/18, 22.1, 24, 26, 30, 34, 36, 134/42, 166 R, 198–201
See application file for complete search history.

(56) References Cited

U.S. PATENT DOCUMENTS

| | | | |
|---|---|---|---|
| 5,289,691 A | 3/1994 | Schlosser et al. | |
| 5,408,834 A | 4/1995 | Schlosser et al. | |
| 5,458,851 A * | 10/1995 | Schroeder et al. | .............. 422/28 |
| 6,698,226 B1 | 3/2004 | Mahloch | |

(Continued)

OTHER PUBLICATIONS

International Search Report from PCT/US2013/53243; 2 pgs.

*Primary Examiner* — Bibi Carrillo
(74) *Attorney, Agent, or Firm* — Andrus Intellectual Property Law, LLP

(57) ABSTRACT

An ice dispensing system includes an ice hopper structure including a plurality of walls having inner surfaces that define an inner volume storing ice therein. The ice hopper may include a drain. A cleaning structure is coupled to the ice hopper structure. The cleaning structure includes a pump linked to a spray mechanism positioned within the inner volume of the ice hopper structure. The spray mechanism disperses a liquid on an inner surface of the ice hopper structure during a cleaning cycle of the ice dispensing mechanism.

5 Claims, 11 Drawing Sheets

Ice Maker & Hopper Sanitization System Schematic

(56) References Cited

U.S. PATENT DOCUMENTS

| | | | |
|---|---|---|---|
| 6,725,675 B2 * | 4/2004 | Kampert et al. | 62/71 |
| 2004/0156263 A1 | 8/2004 | McCann et al. | |
| 2006/0169721 A1 | 8/2006 | Hammonds et al. | |
| 2011/0041542 A1 | 2/2011 | Brunner et al. | |
| 2013/0039808 A1 * | 2/2013 | Erbs et al. | 422/29 |
| 2013/0174875 A1 * | 7/2013 | Walker et al. | 134/22.11 |

* cited by examiner

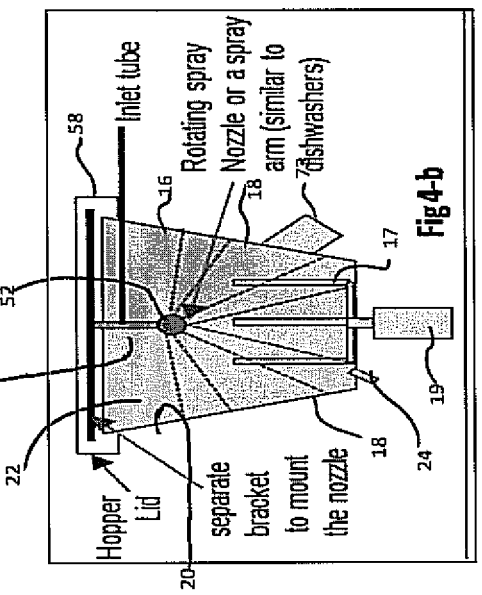
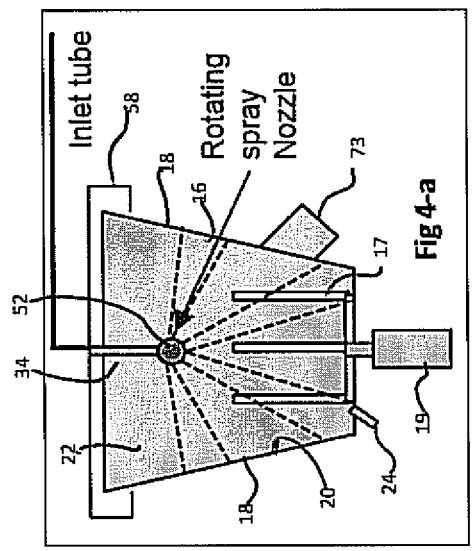

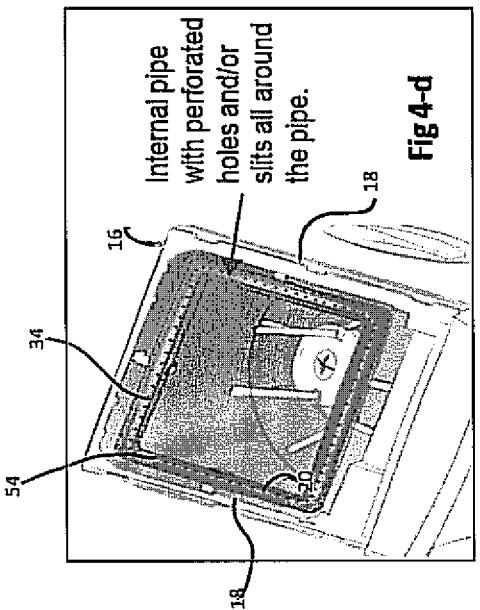
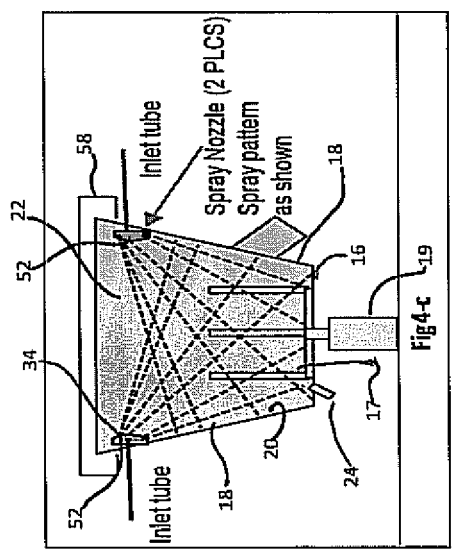

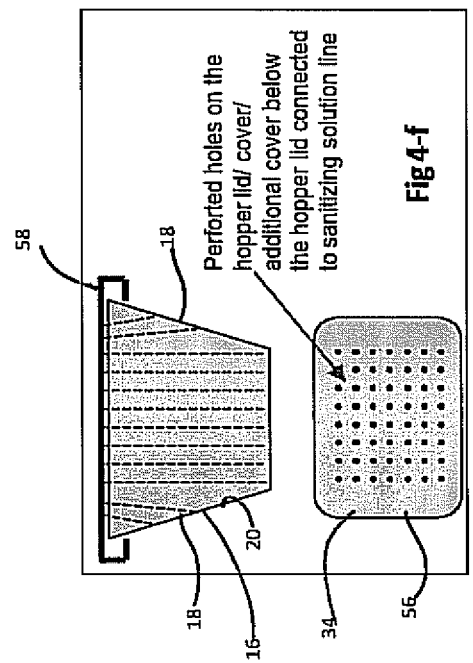
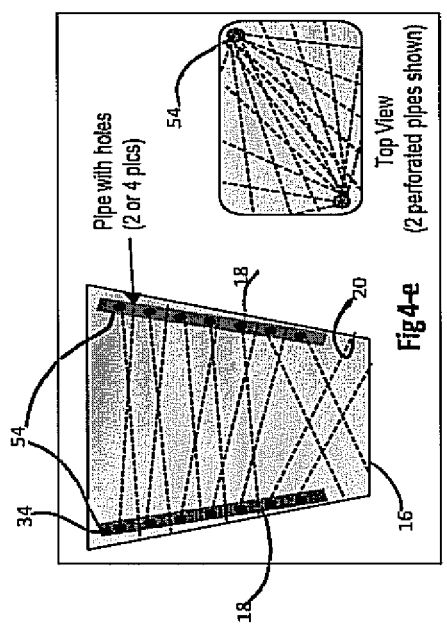

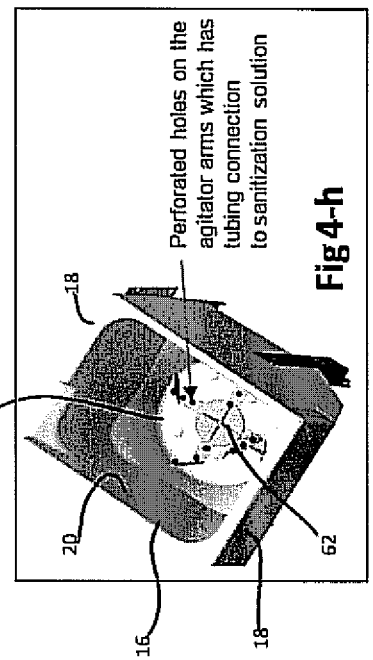
Fig 4-h
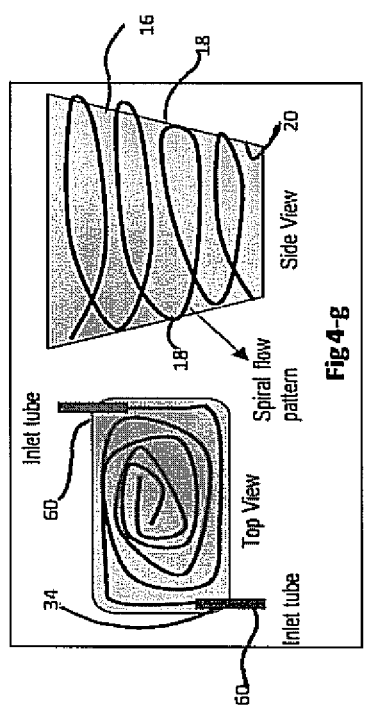
Fig 4-g

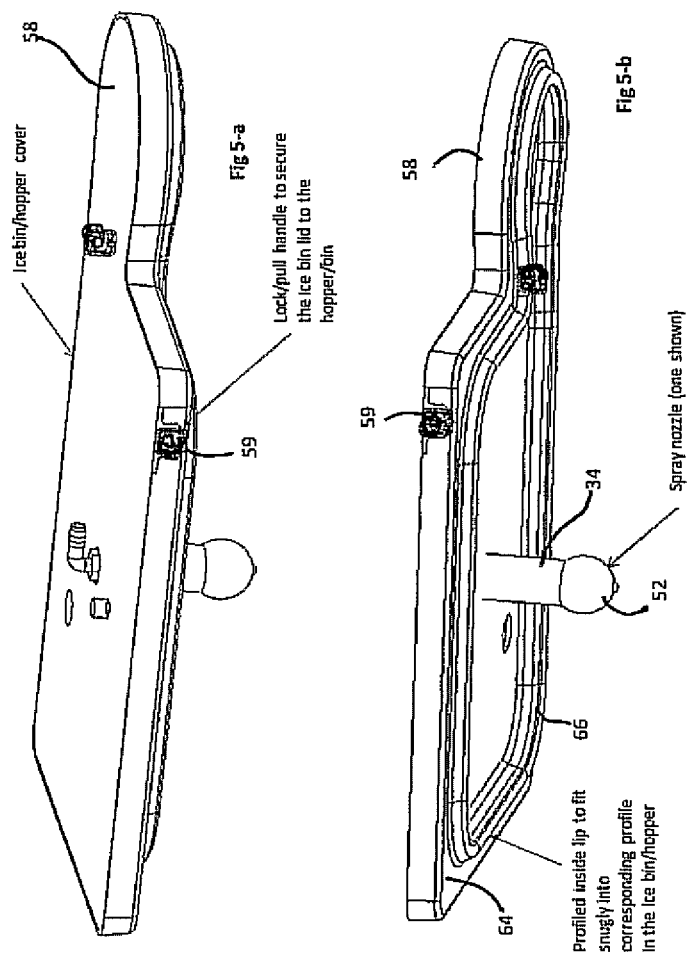

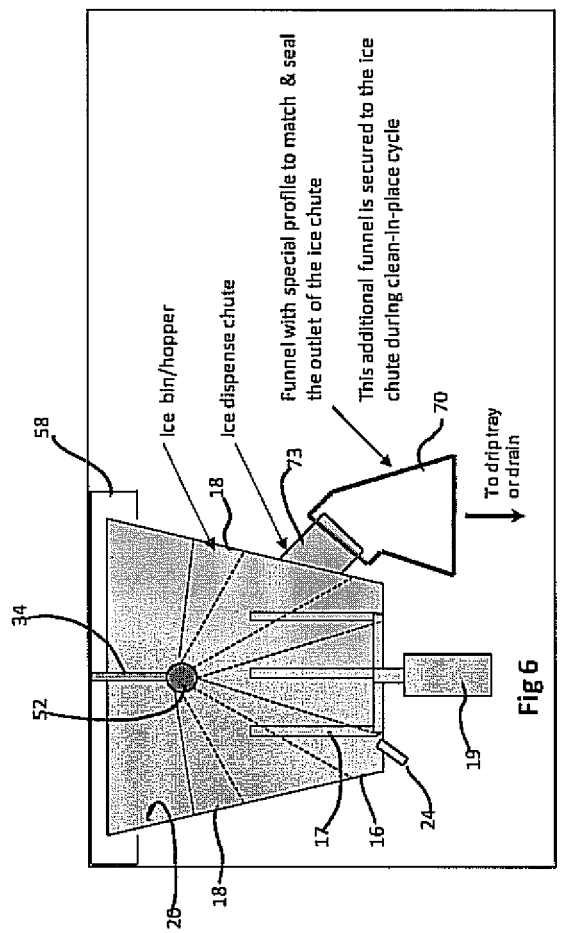

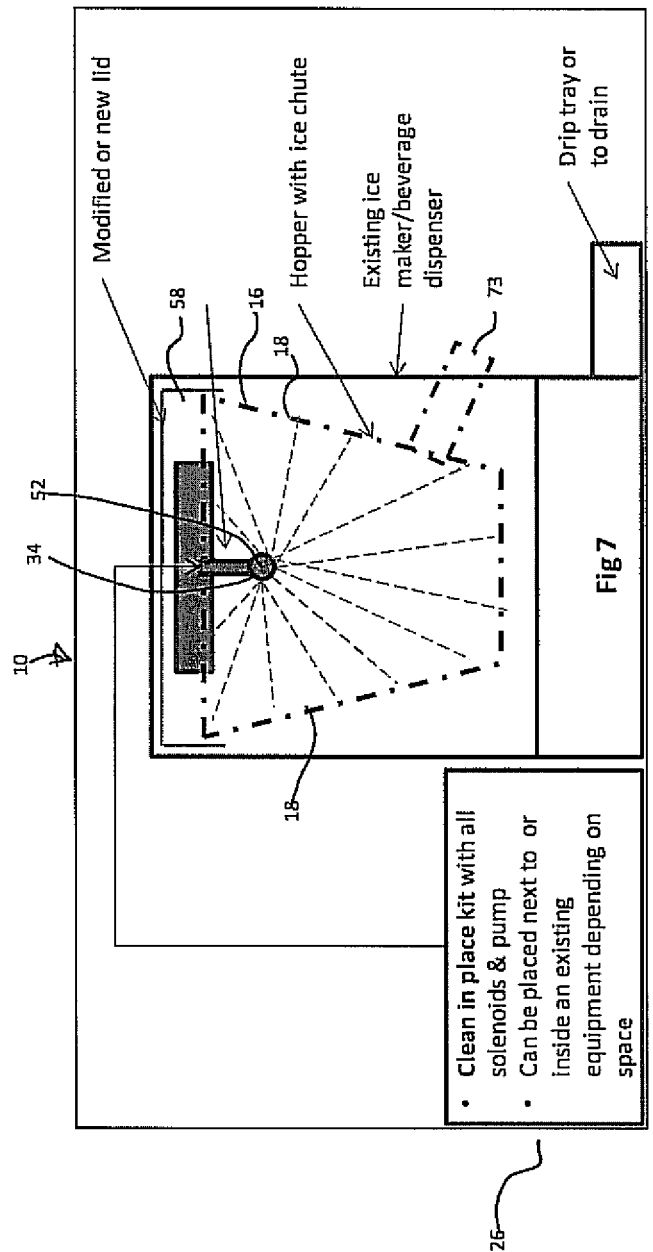

ICE DISPENSING AND CLEANING MECHANISM AND PROCESS

CROSS-REFERENCE TO RELATED APPLICATIONS

This application claims priority of U.S. Provisional Application 61/678,194 filed Aug. 1, 2012, the contents of which are incorporated herein by reference.

FIELD OF THE INVENTION

The invention relates to ice dispensing machines and cleaning systems for cleaning ice dispensing machines.

BACKGROUND OF THE INVENTION

Ice dispensing machines may generate contaminants such as scale and hard water deposits when operating for a long-term duration. Additionally, ice dispensing machines may receive contaminants from an exterior environment such as bacterial or other such contaminants including dust, dirt, and other forms of contamination. Therefore, ice dispensing machines should be cleaned and sanitized at various periodic intervals to assure the quality of ice being produced as well as provide smooth operation of the ice dispensing machine.

Generally, ice dispensing machines may be cleaned and sanitized manually requiring disassembly of various portions of the ice dispensing mechanism. Oftentimes personnel may be required to utilize ladders, disassemble various of the external panels, or require physical ingress into the ice dispensing mechanism such as in the hopper or ice maker portions of such a mechanism.

There is therefore a need in the art for an ice dispensing mechanism that includes a cleaning system that is semi or fully automated and cleans and sanitizes various portions of an ice dispensing mechanism including the ice maker and ice hopper portions of such an assembly. There is also a need in the art for a cleaning system that cleans in place without the requirements for complicated manual operations. There is also a need in the art for such an automated system that may require cleaning of the ice dispensing apparatus at predetermined intervals such that cleanliness and sanitation of the ice dispensing apparatus is maintained.

SUMMARY OF THE INVENTION

In one aspect, there is disclosed an ice dispensing system that includes an ice hopper structure including a plurality of walls having inner surfaces that define an inner volume storing ice therein. The ice hopper may include a drain. A cleaning structure is coupled to the ice hopper structure. The cleaning structure includes a pump linked to a spray mechanism positioned within the inner volume of the ice hopper structure. The spray mechanism disperses a liquid on an inner surface of the ice hopper structure during a cleaning cycle of the ice dispensing mechanism.

In one aspect, there is disclosed an ice dispensing system that includes a water source connected to an ice maker structure. An ice hopper is connected to the ice maker structure. The ice hopper includes a plurality of walls having inner surfaces that define an inner volume storing ice therein. An automated cleaning structure is coupled to the ice maker and ice hopper structures. The automated cleaning structure includes a computer controller and a user interface. The automated cleaning structure includes a pump linked to a spray mechanism positioned within the inner volume of the ice hopper. The spray mechanism disperses a liquid on an inner surface of the ice hopper structure during a cleaning cycle of the ice dispensing mechanism.

In a further aspect, there is disclosed a method of cleaning an ice dispensing system that includes the steps of: providing a water source connected to an ice maker structure; providing an ice hopper structure connected to the ice maker structure, the ice hopper structure including a plurality of walls having inner surfaces that define an inner volume storing ice therein; providing an automated cleaning structure coupled to the ice maker and ice hopper, the automated cleaning structure having a computer controller and a user interface, the automated cleaning structure including a pump linked to a spray mechanism positioned within the inner volume of the ice hopper; removing ice from the ice hopper; running a cleaning and descaling cycle wherein descaling and cleaning solution is introduced into the ice hopper and ice maker; running a sanitizing cycle wherein sanitizing solution is introduced into the ice hopper and ice maker; running a rinsing cycle wherein potable water is introduced into the ice hopper and ice maker wherein the spray mechanism disperses the descaling and cleaning solution, sanitizing solution, and potable water on an inner surface of the ice hopper structure during a cleaning cycle of the ice dispensing mechanism.

BRIEF DESCRIPTION OF THE DRAWINGS

FIGS. 4A-H are structural configurations of the spray mechanism;

FIGS. 5A-B are perspective views of lids that fit over a top opening of the ice hopper;

FIG. 6 is a partial view of an ice hopper including an ice dispense structure having a funnel attached thereon directing liquid from the cleaning operation;

FIG. 7 is a schematic representation of an ice dispensing mechanism including a cleaning structure attached as a kit to the ice dispensing system;

DETAILED DESCRIPTION OF THE PREFERRED EMBODIMENTS

Figure 1:
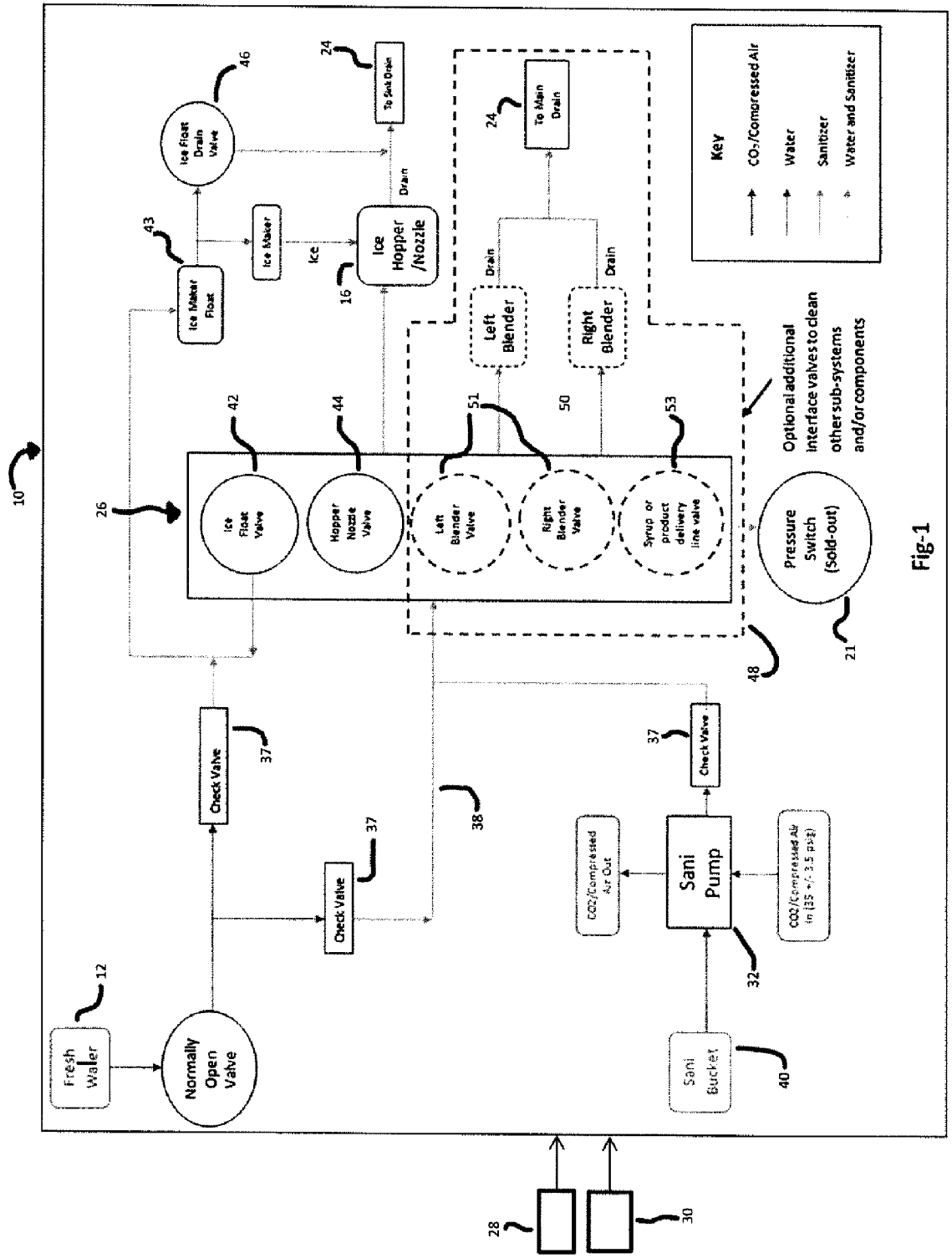
FIG. 1 is a schematic representation of an ice dispensing system including a cleaning structure.

Referring to the Figures, there is shown embodiments of an ice dispensing system 10. The ice dispensing system 10 includes an ice hopper structure 16 including a plurality of walls 18 having inner surfaces 20 that define an inner volume 22 storing ice therein. The ice hopper 16 may include a drain 24. A cleaning structure 26 is coupled to the ice hopper structure 16. The cleaning structure 16 includes a pump 32 linked to a spray mechanism 34 positioned within the inner volume 22 of the ice hopper structure 16. The spray mechanism 34 disperses a liquid on an inner surface 20 of the ice hopper structure 16 during a cleaning cycle of the ice dispensing mechanism. In one aspect, there may be provided a user interface to actuate the pump 32.

Figure 8:
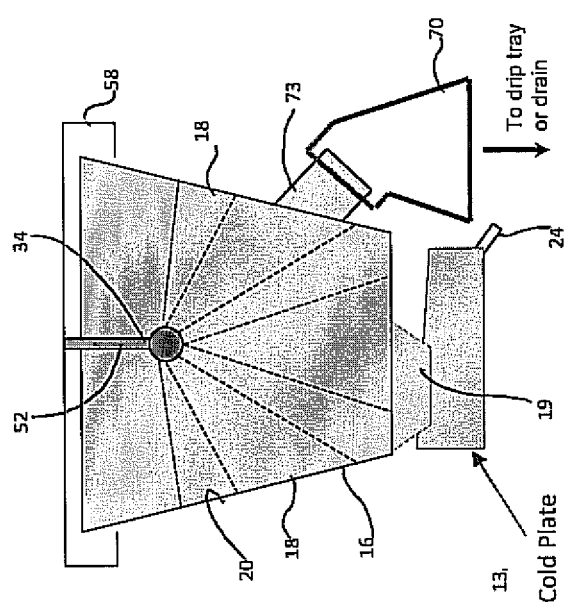
FIG. 8 is a schematic representation of an ice dispensing mechanism including a cold plate.

It should be realized that various types of ice dispensing mechanisms 10 may include the cleaning structure 26 as described above. For example, an ice hopper structure 16 may be linked or connected to an ice maker structure 14, as will be described in more detail below. Alternatively, the ice hopper 16 may be manually filled with ice from an ice source. Additionally, the ice hopper structure 16 may include a cold plate structure 13 as shown in FIG. 8.

Figure 2:
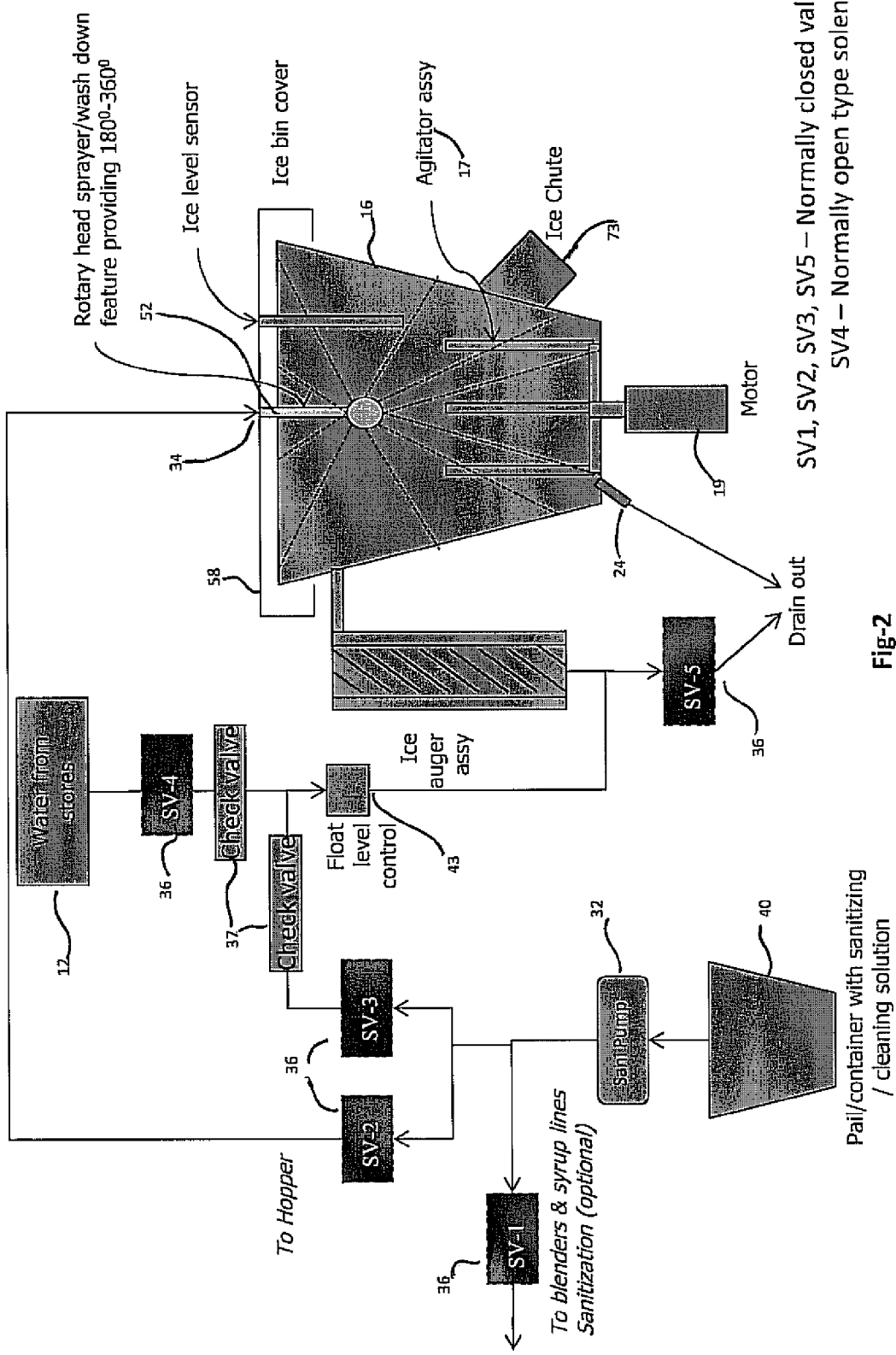
FIG. 2 is a schematic representation of an ice dispensing system including a cleaning structure.

Referring to FIGS. 1 and 2, there are shown schematic representations of an ice dispensing system 10. The ice dispensing mechanism or system 10 includes a water source 12 that is connected to an ice maker structure 14. An ice hopper structure 16 is connected to the ice maker structure 14. The ice hopper structure 16 as best shown in FIGS. 4A-H includes a plurality of walls 18 having inner surfaces 20 that define an inner volume 22 for storing ice therein. In one aspect, the ice hopper 16 includes a drain 24.

An automated cleaning structure 26 is coupled to the ice maker and ice hopper structures 14, 16. The automated cleaning structure 26 includes a computer controller 28 and a user interface 30. The automated cleaning structure 26 includes a pump 32 linked to a spray mechanism 34 that is positioned within the inner volume 22 of the ice hopper 16. The spray mechanism 34 disperses a liquid on inner surfaces 20 of the ice hopper structure 16 during a cleaning cycle of the ice dispensing mechanism 10.

Figure 3:
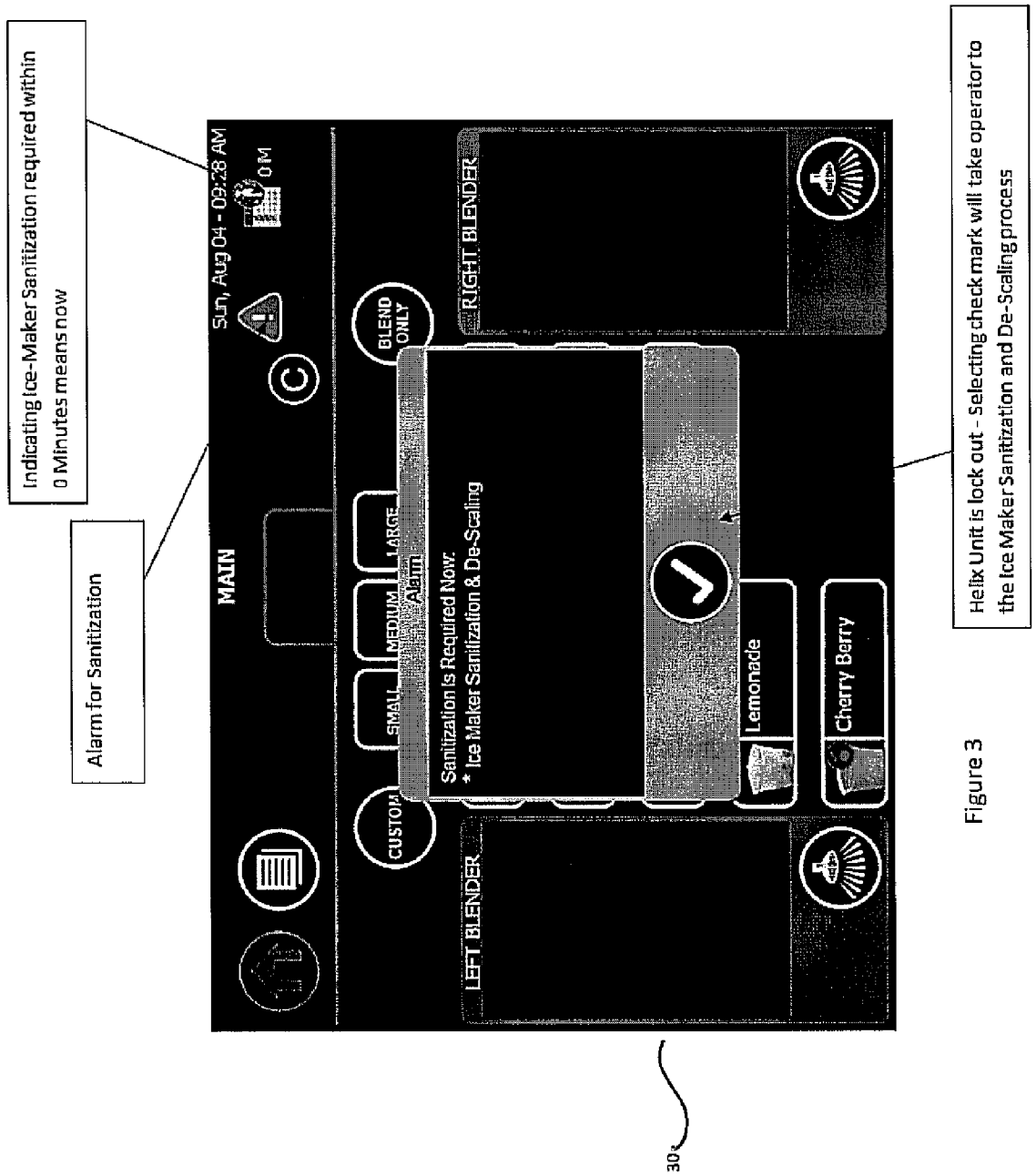
FIG. 3 is a graphic representation of a user interface.

Various user interfaces 30 may be utilized by the automated cleaning structure including touch screens, buttons, toggles, or other mechanisms utilized for controlling and inputting various information associated with the computer controller 28. In the depicted embodiment of FIG. 3, the interface may include a display and touch screen.

In one aspect, the ice dispensing system 10 includes various valves 36 and tubing or lines 38 coupling the various components. In one aspect, the ice dispensing system 10 includes a one way check valve 37 positioned between the water source 12 and the ice maker 14. Another one way check valve 37 may be positioned between a source of cleaning solution 40 and the ice maker 14 and ice hopper 16. In one aspect, the automated cleaning structure 26 includes an external source of a cleaning liquid 40 that is connected to the pump 32. The pump 32 is in turn connected to a one way check valve 37 positioned between the pump 32 and the ice hopper 16 and ice maker 14 structures. In one aspect, a pressure sensor 21 may be linked to the ice dispensing system 10 to verify a pressure of the cleaning solutions or liquids as well as water within the ice dispensing system 10. The pressure sensor 21 may be connected with the computer controller 28 to monitor pressures within the system.

Various other valves including an ice float valve 42 connected to an ice float mechanism 43, an ice hopper nozzle valve 44, and ice float drain valves 46 may be included for supplying water to various of the structures as well as to drain various liquids from the ice dispensing system 10.

In one aspect, the ice dispensing mechanism 10 may include additional beverage dispensing subsystems 48 coupled to the ice dispensing mechanism 10 and connected to the automated cleaning structure 26. In one aspect, as best shown in FIG. 1, the additional beverage subsystem 48 may include a blending station 50 having blender valves 51, ingredient valves 53, and ice hopper valves 44 connected to the ice hopper 16.

Referring to FIGS. 4A-H, there are shown structures of the spray mechanism 34 for dispersing a liquid on inner surfaces 20 of the ice hopper structure 16 during a cleaning cycle of the ice dispensing mechanism 10. In one aspect, as best shown in FIGS. 4A and B, the spray mechanism 34 may include a rotating spray nozzle 52. In another aspect, the spray mechanism 34 may include at least two spray nozzles 52 that are attached to the inner surfaces 20 of the ice hopper 16, as best shown in FIG. 4C. Various spray patterns may be provided by the rotating spray nozzle 52 or at least two spray nozzles 52 attached to the inner surfaces 20 by forming perforated holes within the spray mechanism 34 at desired angles to achieve a coverage of the inner surface of the ice hopper 16.

In another aspect, the spray mechanism 34 may include at least one perforated pipe 54 positioned on an inner surface 20 of the ice hopper 16. Again, the perforated pipe 54 may include holes or slits formed at various angles and positions to achieve a desired spray pattern. The at least one perforated pipe 54 may include a pipe 54 attached about a circumference of the inner surfaces 20 of the ice hopper 16, as shown in FIG. 4D. Alternatively, the at least one perforated pipe 54 may include two perforated pipes 54 attached to the inner surfaces 20 on opposing portions of the ice hopper 16. Again, various holes or slits may be formed at desired positions and angles to achieve a desired spray pattern, as shown in FIG. 4E.

The spray mechanism 34 may include a second cover 56 attached to a lid 58. The secondary cover 56 may include perforations formed therein in various patterns to achieve a desired spray pattern as shown in FIG. 4F.

The spray mechanism 34 may include opposing pipes 60 positioned adjacent the inner surface 20 of the ice hopper 20, as best shown in FIG. 4G. In one aspect, liquid exiting the opposing pipes 60 spirals about the inner surfaces 20 of the ice hopper 20 contacting the surfaces with a liquid.

Referring to FIG. 4H, there is shown an embodiment of a spray mechanism 34 that includes a rotating arm structure 62 attached to an inner surface 20 of the ice hopper 16. In one aspect, the rotating arm 62 may include perforations formed therein to achieve various spray patterns within the inner volume. It should be realized that the rotating arm structure 62 may be attached to various of the inner surfaces with the rotating arm structure attached to a bottom of the inner volume as shown in FIG. 4H.

Referring to FIGS. 5A-B, there is shown a lid 58 that may be positioned over a top opening of the ice hopper 16. In one aspect, the lid 58 includes a bottom surface 64 that has a profile lip 66 extending therefrom in a direction corresponding to the inner volume of the ice hopper 16 when installed. The profile lip 66 may be positioned to contact the inner surfaces 20 of the plurality of walls 18 of the ice hopper 16 forming a liquid-tight seal between the lid 58 and the ice hopper structure 16. In this manner, various gaskets or seals are not needed by the lid 58. In one aspect, the spray mechanism 34 may be connected to the lid 58 or supported from the lid 58 as shown in the figures. In another aspect, the lid 58 may include latches 59 for coupling to the ice hopper 16.

In one aspect, the computer controller 28 of the automated cleaning structure 26 includes a lock out logic in the computer program such that a user must run a cleaning cycle at a predetermined interval or ice will not be dispensed from an ice dispensing mechanism 10. In one aspect, the user interface 30 may display a time to the predetermined interval for the next cleaning cycle. In this manner, compliance with a predetermined cleaning and sanitation regimen is controlled directly by the computer controller 28 associated with the ice dispensing mechanism 10.

In one aspect, the ice dispensing mechanism 10 may include an automated cleaning structure that is an integrated subcomponent of the ice dispensing mechanism 10. In other words, the ice dispensing mechanism 10 may be built with the components of the automated cleaning structure 26 directly attached to or otherwise connected or integrated with the ice dispensing mechanism 10. Alternatively, as best shown in FIG. 7, the automated cleaning structure 26 may be an add-on kit that can be mated to an ice dispensing mechanism 10. In this manner, various ice dispensing mechanisms can be retrofitted or connected with a cleaning structure 26 with the addition of various connections including tubing or valves to allow for the various connections of components.

A method of cleaning an ice dispensing system is also provided. The method includes the steps of providing a water source 12 connected to an ice maker structure 14; providing an ice hopper structure 16 connected to the ice maker structure 14, the ice hopper structure 16 including a plurality of walls 18 having inner surfaces 20 that define an inner volume 22 storing ice therein, the ice hopper 16 including a drain 24; providing an automated cleaning structure 26 coupled to the ice maker and ice hopper structures 14, 16, the automated cleaning structure 26 having a computer controller 28 and a user interface 30, the automated cleaning structure 26 including a pump 32 linked to a spray mechanism 34 positioned within the inner volume 22 of the ice hopper 16; removing ice from the ice hopper 16; running a cleaning and descaling cycle wherein descaling and cleaning solution is introduced into the ice hopper 16 and ice maker 14; running a sanitizing cycle wherein sanitizing solution is introduced into the ice hopper 16 and ice maker 14; running a rinsing cycle wherein potable water is introduced into the ice hopper 16 and ice maker 14 wherein the spray mechanism 34 disperses the descaling and cleaning solution, sanitizing solution, and potable water on an inner surface 20 of the ice hopper structure 16 during a cleaning cycle of the ice dispensing mechanism.

In one aspect, the method may include the step of positioning a funnel structure 70 about an ice dispense nozzle 73 for directing liquid from the cleaning cycle to a drain 24, as best shown in FIG. 6.

In one aspect, the step of running a cleaning and descaling cycle may include the steps of: preparing a cleaning and descaling solution in an exterior vessel 40; positioning a sanitary tube 72 into the vessel 40 with the sanitary tube 72 connected to the pump 32; actuating a cycle start of the user interface 30; draining water from the ice maker 14; introducing cleaning and descaling solution into the ice maker 14 and maintaining the solution in position for a predetermined time; spraying cleaning and descaling solution on the inner surfaces 20 of the ice hopper 16; forming ice from the cleaning and descaling solution in the ice maker 14; discarding the ice from the ice maker 14; and draining the cleaning and descaling solution from the ice maker 14 and ice hopper 16.

In one aspect, the step of running a sanitizing cycle may include the steps of: preparing a sanitizing solution in an exterior vessel 40; positioning a sanitary tube 72 into the vessel 40 with the sanitary tube connected to a pump 32; introducing sanitizing solution into the ice maker 14 and maintaining the sanitizing solution in position for a predetermined time; spraying sanitizing solution on the inner surfaces 20 of the ice hopper 16; forming ice from the sanitizing solution in the ice maker 14; discarding the ice from the ice maker 14; and draining the sanitizing solution from the ice maker 14 and ice hopper 16. In one aspect, the step of air drying the ice hopper 16 may be performed following the step of running a sanitizing cycle.

In one aspect, the step of running a rinsing cycle may include the steps of preparing a source of potable water in an exterior vessel 40; positioning a sanitary tube 72 into the vessel 40 with the sanitary tube 72 connected to a pump 32; introducing potable water into the ice maker 14 and maintaining the potable water in position for a predetermined time; spraying potable water on the inner surfaces 20 of the ice hopper 16; forming ice from the potable water in the ice maker 14; discarding the ice from the ice maker 14; and draining the potable water from the ice maker 14 and ice hopper 16. In one aspect, the step of running a dry cycle following the step of rinsing may be performed. In one aspect, the step of performing a dry cycle may include removing a sanitary tube 72 from the vessel 40 and providing a source of air to the pump, such that the pump forces air through the ice hopper 16, ice maker 14, and automated cleaning structure 26 flushing liquid from the ice dispensing system 10.

The invention has been described in an illustrative manner. It is to be understood that the terminology which has been used is intended to be in the nature of words of description rather than limitation. Many modifications and variations of the invention are possible in light of the above teachings. Therefore, within the scope of the appended claims, the invention may be practiced other than as specifically described.

The invention claimed is:

1. A method of cleaning an ice dispensing system, the method comprising:

providing a water source connected to an ice maker structure;

providing an ice hopper structure connected to the ice maker structure, the ice hopper structure including a plurality of walls having inner surfaces that define an inner volume storing ice therein, the ice hopper including a drain;

providing an automated cleaning structure coupled to the ice maker and ice hopper structures, the automated cleaning structure having a computer controller and a user interface, the automated cleaning structure including a pump linked to a spray mechanism positioned within the inner volume of the ice hopper, removing ice from the ice hopper;

running a cleaning and descaling cycle wherein a descaling and cleaning solution is introduced into the ice hopper and ice maker;

running a sanitizing cycle wherein a sanitizing solution is introduced into the ice hopper and ice maker;

running a rinsing cycle wherein potable water is introduced into the ice hopper and ice maker;

wherein the spray mechanism disperses the descaling and cleaning solution, sanitizing solution and potable water on an inner surface of the ice hopper structure;

wherein running a cleaning and descaling cycle comprises:

preparing a cleaning and descaling solution in an exterior vessel;

positioning a sanitary tube into the vessel, said sanitary tube connected to said pump;

starting the cleaning and descaling cycle;

draining water from the ice maker;

introducing the cleaning and descaling solution into the ice maker and maintaining the cleaning and descaling solution in position for a predetermined time;

spraying the cleaning and descaling solution on the inner surfaces of the ice hopper; forming ice from the cleaning and descaling solution in the ice maker; discarding the ice from the ice maker; and draining the cleaning and descaling solution from the ice maker and ice hopper.

2. The method of claim 1 including the step of positioning a funnel structure about an ice dispense nozzle for directing liquid to a drain.

3. The method according to claim 1 further comprising air drying the ice hopper following the step of running the sanitizing cycle.

4. A method of cleaning an ice dispensing system, the method comprising:

providing a water source connected to an ice maker structure;

providing an ice hopper structure connected to the ice maker structure, the ice hopper structure including a plurality of walls having inner surfaces that define an inner volume storing ice therein, the ice hopper including a drain;

providing an automated cleaning structure coupled to the ice maker and ice hopper structures, the automated cleaning structure having a computer controller and a user interface, the automated cleaning structure including a pump linked to a spray mechanism positioned within the inner volume of the ice hopper, removing ice from the ice hopper;

running a cleaning and descaling cycle wherein a descaling and cleaning solution is introduced into the ice hopper and ice maker;

running a sanitizing cycle wherein a sanitizing solution is introduced into the ice hopper and ice maker;

running a rinsing cycle wherein potable water is introduced into the ice hopper and ice maker;

wherein the spray mechanism disperses the descaling and cleaning solution, sanitizing solution and potable water on an inner surface of the ice hopper structure;

wherein running a sanitizing cycle comprises:

preparing a sanitizing solution in an exterior vessel;

positioning a sanitary tube into the vessel, said sanitary tube connected to said pump;

introducing the sanitizing solution into the ice maker and maintaining the sanitizing solution in position for a predetermined time;

spraying the sanitizing solution on the inner surfaces of the ice hopper;

forming ice from the sanitizing solution in the ice maker;

discarding the ice from the ice maker; and draining the sanitizing solution from the ice maker and ice hopper.

5. A method of cleaning an ice dispensing system, the method comprising:

providing a water source connected to an ice maker structure;

providing an ice hopper structure connected to the ice maker structure, the ice hopper structure including a plurality of walls having inner surfaces that define an inner volume storing ice therein, the ice hopper including a drain;

providing an automated cleaning structure coupled to the ice maker and ice hopper structures, the automated cleaning structure having a computer controller and a user interface, the automated cleaning structure including a pump linked to a spray mechanism positioned within the inner volume of the ice hopper;

removing ice from the ice hopper;

running a cleaning and descaling cycle wherein a descaling and cleaning solution is introduced into the ice hopper and ice maker;

running a sanitizing cycle wherein a sanitizing solution is introduced into the ice hopper and ice maker;

running a rinsing cycle wherein potable water is introduced into the ice hopper and ice maker;

wherein the spray mechanism disperses the descaling and cleaning solution, sanitizing solution, and potable water on an inner surface of the ice hopper structure;

wherein running a rinsing cycle comprises:

preparing a source of potable water in an exterior vessel;

positioning a sanitary tube into the vessel, said sanitary tube connected to said pump;

introducing the potable water into the ice maker and maintaining the potable water in position for a predetermined time;

spraying the potable water on the inner surfaces of the ice hopper;

forming ice from the potable water in the ice maker;

discarding the ice from the ice maker;

draining the potable water from the ice maker and ice hopper; and further comprising running a dry cycle following the step of running the rinsing cycle, wherein the dry cycle includes removing the sanitary tube from the vessel; and providing a source of air to the pump, the pump forcing air through the ice hopper, ice maker, and automated cleaning structure, thereby flushing the ice dispensing system of liquid.

* * * * *